(12) United States Patent
Cheng et al.

(10) Patent No.: US 11,083,437 B2
(45) Date of Patent: Aug. 10, 2021

(54) METHOD AND DEVICE FOR IN SITU CANCER MARGIN DETECTION

(71) Applicant: Purdue Research Foundation, West Lafayette, IN (US)

(72) Inventors: Ji-xin Cheng, West Lafayette, IN (US); Pu Wang, West Lafayette, IN (US); Lu Lan, West Lafayette, IN (US); Rui Li, West Lafayette, IN (US)

(*) Notice: Subject to any disclaimer, the term of this patent is extended or adjusted under 35 U.S.C. 154(b) by 303 days.

(21) Appl. No.: 15/772,630

(22) PCT Filed: Nov. 2, 2016

(86) PCT No.: PCT/US2016/060062
§ 371 (c)(1),
(2) Date: May 1, 2018

(87) PCT Pub. No.: WO2017/079253
PCT Pub. Date: May 11, 2017

(65) Prior Publication Data
US 2019/0117197 A1    Apr. 25, 2019

Related U.S. Application Data

(60) Provisional application No. 62/249,747, filed on Nov. 2, 2015, provisional application No. 62/295,028, filed on Feb. 13, 2016.

(51) Int. Cl.
*A61B 8/08*    (2006.01)
*A61B 8/00*    (2006.01)
*A61B 5/00*    (2006.01)

(52) U.S. Cl.
CPC .......... *A61B 8/5223* (2013.01); *A61B 5/0095* (2013.01); *A61B 8/085* (2013.01); *A61B 8/0825* (2013.01); *A61B 8/4281* (2013.01); *A61B 8/4416* (2013.01); *A61B 2505/05* (2013.01); *A61B 2576/02* (2013.01)

(58) Field of Classification Search
CPC ... A61B 5/0095; A61B 8/5223; A61B 8/0825; A61B 8/085; A61B 8/4281; A61B 8/4416
See application file for complete search history.

(56) References Cited

U.S. PATENT DOCUMENTS

| | | | | |
|---|---|---|---|---|
| 2002/0191503 A1* | 12/2002 | Kataoka | ............... | G11B 7/08511 369/44.29 |
| 2008/0221647 A1* | 9/2008 | Chamberland | ...... | A61N 5/0601 607/88 |
| 2013/0158383 A1* | 6/2013 | Cheng | .................. | A61B 5/0095 600/407 |
| 2013/0165765 A1* | 6/2013 | Nishihara | ............ | A61B 8/0825 600/407 |

(Continued)

*Primary Examiner* — Helen C Kwok
(74) *Attorney, Agent, or Firm* — Gutwein Law; Tyler B. Droste

(57) ABSTRACT

A multimodal ultrasound/photoacoustic tumor margin detection system. The system can be comprised of an imaging and system control console, which can include an ultrasound and data acquisition subsystem including an ultrasound transmitter and receiver configured to transmit and receive ultrasonic energy. A host-control computer configured to provide a function generator function and a delay generation function can also be a part of the imaging and system control console.

20 Claims, 11 Drawing Sheets

(56) References Cited

U.S. PATENT DOCUMENTS

| | | | | |
|---|---|---|---|---|
| 2013/0276542 A1* | 10/2013 | Herzog | ............... | A61B 5/0073 |
| | | | | 73/655 |
| 2014/0200434 A1* | 7/2014 | Cheng | .................. | A61B 5/0095 |
| | | | | 600/407 |
| 2014/0323860 A1* | 10/2014 | Courtney | ............... | A61B 8/445 |
| | | | | 600/427 |
| 2014/0336261 A1* | 11/2014 | Chin | ....................... | A61P 35/00 |
| | | | | 514/604 |
| 2014/0340685 A1* | 11/2014 | Kim | .................. | G01N 29/2418 |
| | | | | 356/432 |
| 2015/0031990 A1* | 1/2015 | Boctor | ................ | A61B 8/5261 |
| | | | | 600/424 |
| 2017/0156600 A1* | 6/2017 | Ntziachristos | ......... | A61B 5/441 |
| 2017/0236275 A1* | 8/2017 | Jung | ................... | A61B 6/5217 |
| | | | | 382/131 |
| 2017/0363582 A1* | 12/2017 | Mertz | ............... | G01N 29/0681 |

* cited by examiner

METHOD AND DEVICE FOR IN SITU CANCER MARGIN DETECTION

CROSS-REFERENCE TO RELATED APPLICATION

This U.S. Patent Application claims priority to U.S. Provisional Application 62/249,747 filed Nov. 2, 2015, and U.S. Provisional Application 62/295,028 filed Feb. 13, 2016 the disclosures of which is considered part of the disclosure of this application and is hereby incorporated by reference in its entirety.

FIELD OF THE INVENTION

The present application relates to optical detection systems and in particular to a photoacoustic detection system that can be used in surgical procedures.

BACKGROUND

This section introduces aspects that may help facilitate a better understanding of the disclosure. Accordingly, these statements are to be read in this light and are not to be understood as admissions about what is or is not prior art.

As with all cancers, early diagnosis and treatment including surgical excision are chief amongst improving survival chances. Confirmation of the tumor removal during cancer surgery is critical for lowering the recurrence rate and hence increase the outcome for the patients. Such confirmation is usually done by post-surgical histopathology or intraoperative pathology, which are time consuming and labor intensive. It is a challenge for most surgeries of solid tumors, such as breast cancer, brain cancer, skin cancer, kidney cancer, and liver cancer etc.

For example, breast-conserving surgery, or lumpectomy, is well accepted for breast cancer treatment. To prevent local cancer recurrence after lumpectomy, histology is performed to check whether the excised tumor specimen is surrounded by a sufficient amount of normal tissue. If a positive margin, i.e., less than about 2 mm between the surfaces of the excised specimen to the tumor, is identified, then a second operation will be performed to minimize the chance of cancer recurrence. Currently, the re-operation rate ranges from about 20 to about 70 percent. Such high re-operation rate highlights a critical need for rapid and highly sensitive intraoperative margin assessment.

From a clinical perspective, examining the excised specimen is the standard of care, whether performed intraoperatively or postoperatively. The major criteria for designing an intraoperative margin assessment tool of the excised tissue are: 1) high sensitivity: closely matching the histological result; 2) high speed: obtaining the result in less than 20 min; 3) Deep tissue penetration: imaging up to 2 mm deep in tissue; 4) large sampling area: detecting the entire margin surface; 5) removing the need for interpretation from pathologists. Table 1 summarizes the current and emerging technologies for ex vivo intraoperative margin assessment, and specifies their speed, sensing depth, resolution, sensitivity and specificity.

Cytological examination and frozen section are widely applied clinically, but these two methods suffer from long procedure time and low sensitivity owing to the sampling method. Radio frequency spectroscopy reduces the procedure time, but suffers from the sensitivity and specificity due to the lack of chemical selectivity. Intraoperative ultrasound imaging has been applied to guide lumpectomies but with poor chemical selectivity. Emerging optical technologies, including diffuse reflectance imaging, optical coherence tomography and spatial offset Raman spectroscopy, have greatly improved the sensitivity and specificity but still suffer from long procedure time, shallow tissue penetration, or an inability to assess the entire tumor tissue. Near infrared fluorescence imaging technology has been reported for in vivo breast tumor removal. This technique requires exogenous labels to specific cancer targets, raising issues of labeling efficiency, toxicity, and regulatory burden. Diffuse optical tomography has also been reported for in vivo breast tumor imaging. However, it suffers from poor depth resolution due to a dramatic decrease in depth sensitivity. Therefore, an unmet need exists in developing an intraoperative device that is rapid, sensitive, label-free, and able to scan the entire tissue surface for accurate breast cancer margin assessment.

There is, therefore an unmet need for a novel arrangement that can offer a high-speed and highly-sensitive intraoperative assessment of breast cancer margin during conservation surgical procedures.

BRIEF SUMMARY OF THE INVENTION

In one aspect, this disclosure is related to a multimodal ultrasound/photoacoustic tumor margin detection system. The system can be comprised of an imaging and system control console, which can include an ultrasound and data acquisition subsystem including an ultrasound transmitter and receiver configured to transmit and receive ultrasonic energy. A host-control computer configured to provide a function generator function and a delay generation function can also be a part of the imaging and system control console.

A laser subsystem, can be comprised of at least one laser that can be coupled to a fiber bundle which can be coupled an imaging probe. The laser subsystem can further comprise a quarter wave plate and a half wave plate, wherein the half wave plate and polarizer are configured to adjust optical energy, and wherein the quarter wave plate is configured to protect the laser from back-reflection. The laser subsystem can also use a plurality of mirrors. In one embodiment six mirrors can be used in the laser subsystem. The laser subsystem can comprise a crystal that serve as wavelength converter. The conversion mechanism can be optical parametric oscillation effect, Raman effect, or Brillouin effect.

The imaging probe can be comprised of an ultrasound transducer configured to be excited by the ultrasound transmitter of the ultrasound and data acquisition subsystem and provide data to the ultrasound receiver of the ultrasound and data acquisition subsystem. An optical channel coupled to the fiber bundle, can be configured to provide optical energy to a tissue under investigation. The imaging probe can be side-firing or forward firing. The propagation of the optical energy can be collinearly aligned with the propagation of the ultrasound energy.

The apparatus can have a scanning stage configured to hold the either the tissue or the imaging probe for interrogation, wherein the optical energy and ultrasound energy generate a multimodal dataset for generating an image of the tissue. The images can be 2D cross-sectional image or 3D volumetric image. The tissue can be placed or fixed inside a cartridge and covered or sub-merged within ultrasound coupling medium. The medium can be water or gel.

In yet another aspect, this disclosure is related to a method of ultrasonic/photoacoustic imaging of tissue and determining the margin status of excised tissue. The method can comprise the steps of fixing said tissue in a cartridge using a coupling medium. A first scanning of the first face of the tissue can be carried out. The first scanning can comprise photoacoustically stimulating said tissue with a optical energy via an imaging probe comprising a laser comprising a fiber bundle, at least one cylindrical lens, and at least one glass slide. The photoacoustic signals generated from the tissue can then be captured via a transducer array proximately placed near the tissue. Ultrasonic pulses can then be transmitted into the tissue via the ultrasound transducer to a first focus spot at a pre-determined depth of the tissue.

The ultrasonic signals generated from the tissue can then be captured via the transducer array. The focus spot of the tissue can then be repositioned relative to the ultrasound transduce by a pre-determined distance and direction. The repositioning can be repeated a pre-determined number of times, wherein each time ultrasonic pulses are transmitted and captured via the transducer array. An image can then be generated of the tissue by combining the various ultrasonic and photoacoustic signals from the first scanning.

In some embodiments, the tissue sample can be rotated 180 degrees relative to the transducer and a second scanning of a second side of the tissue sample can be carried out. The signal from the first and second scanning can be combined to generate an image of the tissue. In some embodiments the image can be three dimensional in nature. Furthermore, an algorithm can process the image or images generated to further classify portions of the tissue as tumorous or non-tumorous based on the captured photoacoustic and ultrasonic signals.

In yet another aspect, this disclosure relates to an in situ margin detection sample imaging system comprising an imaging probe and imaging chamber. The imaging probe can include an ultrasound transducer configured to be excited by the ultrasound transmitter of the ultrasound and data acquisition subsystem and provide data to the ultrasound receiver of the ultrasound and data acquisition subsystem. The imaging probe can also comprise an optical channel coupled to the fiber bundle, configured to provide optical energy to a tissue under investigation. Additionally, a scanning stage configured to hold the tissue or the imaging probe for interrogation can be provided. The optical energy and ultrasound energy can generate a multimodal dataset for generating an image of the tissue. Specific tissue types can be identified by the ultrasound image and the photoacoustic image. A computer system can use an algorithm to further classify portions of the tissue sample as tumorous or non-tumorous.

BRIEF DESCRIPTION OF THE DRAWINGS

The features and advantages of this disclosure, and the manner of attaining them, will be more apparent and better understood by reference to the following descriptions of the disclosed system and process, taken in conjunction with the accompanying drawings, wherein.

DETAILED DESCRIPTION OF THE INVENTION

Figure 1:
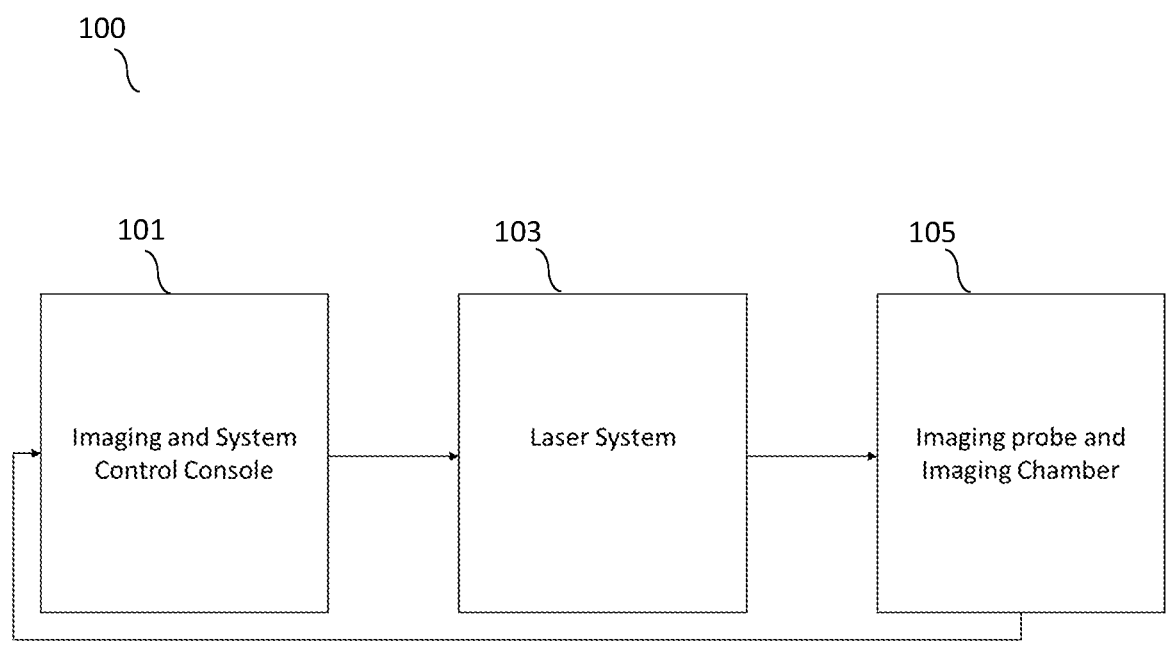
FIG. 1 is a block diagram of an exemplary environment of a multimodal ultrasonic and photoacoustic imaging system.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

A novel arrangement that can offer a high-speed and highly-sensitive intraoperative assessment of breast cancer margin during conservation surgical procedures is disclosed herein. In particular, a multi-modal ultrasound/photoacoustic (US/PA) imaging system for highly sensitive breast cancer margin assessment is presented. Photoacoustic tomography (PAT) has proved its capability of rapid deep tissue imaging with chemical selectivity. It also incorporates an ultrasound imaging modality. With hemoglobin, adipose tissue, and photoacoustic contrast agents as the contrast, the PAT of the present disclosure can be applied in breast cancer imaging for surgical planning, as well as other imaging and surgical procedures.

One primary issue with current technology is the sole contrast from blood cannot sensitively determine a margin status. This is due to the fact that hemoglobin mainly presents in angiogenesis process in invasive cancer but not in ductal carcinoma in situ. PA imaging through the excitation at ~1200 nm, can allow for fat to be visualized, providing a new contrast to assist margin assessment, especially with regards to imaging of breast due to fat being the major form of normal tissue in breast. Beyond the PA mode, a radio frequency (RF) spectrum analysis of US signal can be implemented to further assist the diagnosis. RF spectral analysis of an US can be demonstratively used to quantitatively differentiate tissue types in ultrasound imaging based on the differences in tissue mechanical properties. According to the present disclosure, the use of contrasts from RF spectrum analysis of US and PAT together are shown to synergistically enhance the tumor assessment sensitivity and specificity. This multi-contrast system can obtain comprehensive tissue-specific information, and thus it can achieve better sensitivity and specificity compared to the abovementioned single contrast techniques.

Accordingly, deep tissue sensing of greater than about 3 mm, high speed imaging with about 2 minutes to cover about 40 cm² area, and free from exogenous labeling have been demonstrated. Those specifications exactly match the requirement of intraoperative margin assessment, which is beyond the reach by current platforms.

Referring to FIG. 1, a high-level block diagram for an exemplary embodiment of a multimodal ultrasound/photoacoustic (US/PA) arrangement according to the present disclosure is provided. The arrangement can include an imaging and system control console block 101, a laser subsystem block 103 communicatively coupled to the imaging and system control console block 101, and a imaging probe and imaging chamber block 105 coupled to the laser subsystem block 103, which is also communicatively coupled to the imaging and system control console block 101.

Figure 2A:
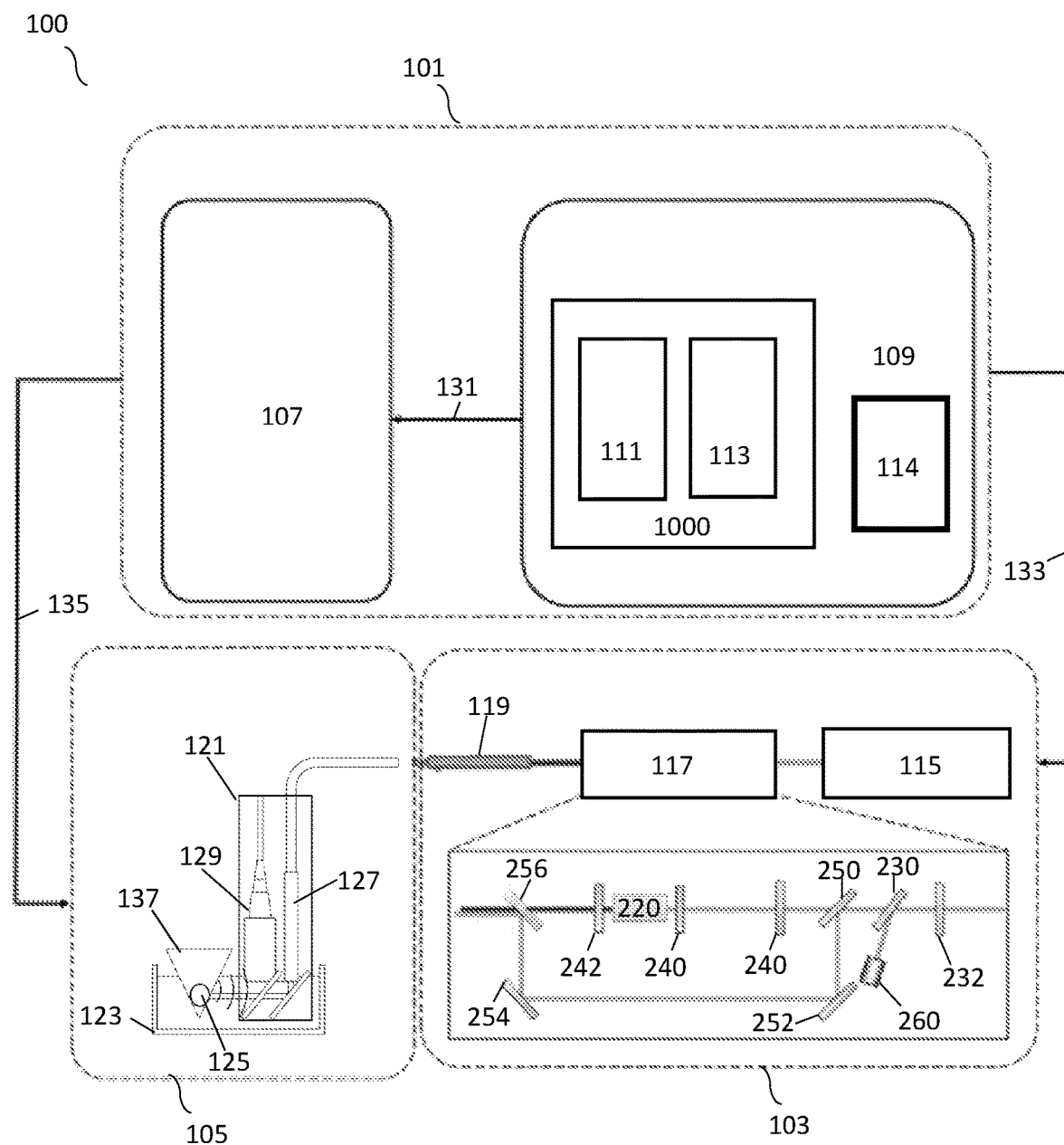
FIG. 2A is a schematic illustration of an exemplary environment of a multimodal ultrasonic and photoacoustic imaging system.
Figure 2B:
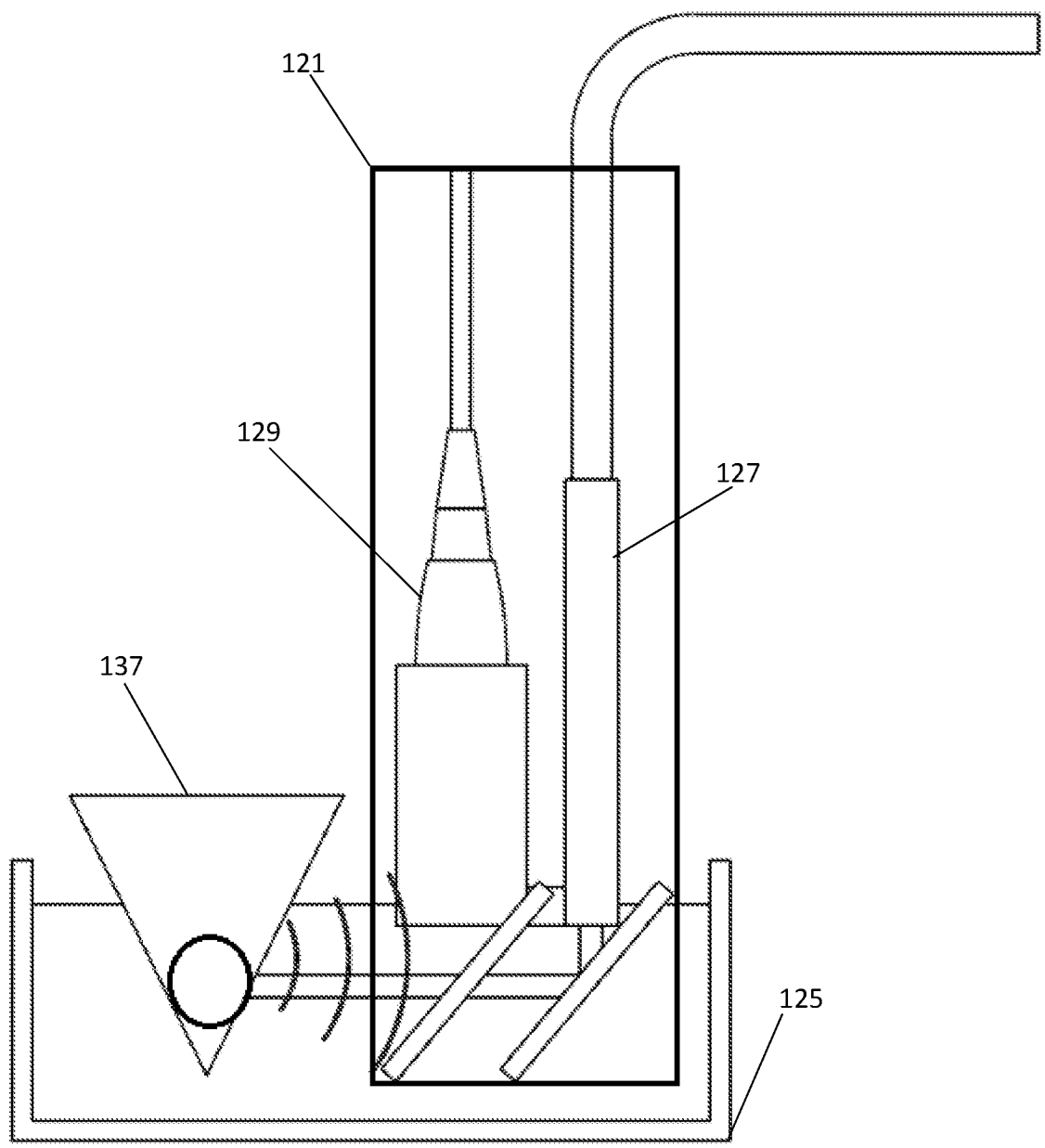
FIG. 2B is an illustration of an exemplary embodiment of an imaging chamber.

Referring to FIG. 2A-B, a more detailed schematic of FIG. 1 is presented. The imaging and system control console 101 block includes two parts: ultrasound source and data acquisition subsystem 107, and the system control console 109 comprising a host-control computer 1000 incorporating a function generator 111 and delay generator 113. The two components can be connected through any suitable connector 131, such as a PCIe cable. The ultrasound source and data acquisition subsystem 107 can act as both ultrasound emitter and receiver, which allows dual modality traditional ultrasound and photoacoustic imaging. In one embodiment, for example only, the ultrasound source and data acquisition subsystem fulfills 128-channel information interchange, 65 MHz sampling rate, 100 μm ultrasound resolution, and 150 μm photoacoustic resolution. The host-control computer 1000 can also be comprised of a user interface 114, for image reconstruction and outputting test results. The host-control computer 1000 can also incorporate a function generator 111 and a delay generator 113 can synchronize pulse excitation and signal acquisition.

The system control console 109 can be communicatively coupled to the laser subsystem using any suitable connector 133. The laser subsystem 103 block includes a light source, such as a laser 117 to be used as a light excitation source. One exemplary embodiment can use a customized Nd:YAG pumped Raman laser 115, similar to that disclosed in the U.S. Pat. No. 9,257,928, herein incorporated by reference. The schematic of one exemplary embodiment of a Raman laser 117 is shown in FIG. 2A. The half wave plate 232 and following polarizer 230 can be used to adjust the laser energy. A dump 260 can be used to collect light reflected off of the polarizer 230. The quarter wave plate 258 plays the role of protecting the Nd:YAG laser 115 from back-reflection. Mirrors can be positioned throughout the laser subsystem in a suitable arrangement and at suitable orientations. In one exemplary embodiment, the Raman laser 117, can have a resonator end mirror 240 that can be coated with high reflectivity at 1197 nm (R>99%) and high transmission at 1064 nm. An output coupler 242 can be coated with high reflectivity at 1064 nm (R>99%) and 40% transmission at 1197 nm. It is understood, that other reflectivity coatings can be used on the mirrors to meet various imaging needs by a user.

A crystal 220 can be arranged within the cavity of the laser. One type of crystal can be a Ba(NO₃)₂ crystal and can have dimensions of about 4 mm×4 mm×38 mm, and coated with high transmission at 1064 nm and 1197 nm on both faces. Mirrors 250, 252, 254, 256 can be positioned at 45 degrees and be 1064 nm reflective mirrors. As previously mentioned two mirrors 240, 242 on each end of the Raman crystal, can have a special coating on the mirrors and, which can act as a cavity for Ba(NO₃)₂ Raman crystal. Mirrors 250 and 256 can be placed in motorized flipper mount, thereby allowing for 1064 nm and 1197 nm output to be switched as desired by a user via a hand-held control pad of the system control console 109 that can be communicatively coupled to the laser subsystem 103. The laser output can be directly coupled into an optical fiber bundle 119, wherein one embodiment, the optical fiber bundle 119 can have about a 1 cm diameter. The optical fiber bundle 119 can also have two distal terminals, which in some embodiments can be rectangular with dimensions about 12 mm by about 2 mm. The terminals can be stabilized in parallel with the ultrasound transducer 129 on each side. The optical fiber bundle 119 can be communicatively coupled to the imaging probe 121.

The imaging probe 121 can be comprised of at least one ultrasound transducer 129 and a fiber bundle holder 127. In some embodiment, the ultrasound transducer can be comprised of a plurality of transducer arrays. The imaging probe 121 can be used to image a tissue sample located within the sample cartridge 137. The sample cartridge 137 can be placed on the sample stage 123. The sample cartridge 137 can be any suitable shape, in one exemplary embodiment the sample cartridge is pyramidal in shape. All the optical components covered by an enclosure can be placed through optical posts and optical post holders on the circuit board. The particular optical devices identified here are for demonstration purposes and the scope of the disclosure should not be limited to these devices.

FIG. 2B is an illustration of an exemplary embodiment of an imaging probe 121 for a sample cartridge 137 and imaging chamber 105. In one exemplary embodiment, the imaging probe 121 and imaging chamber 105 block can be comprised of an ultrasound transducer 129, one or two fiber bundle terminals 127, the scanning stage 123, and a sample cartridge 137. Upon laser light excitation from the fiber bundle terminals, the ultrasound waves are generated from the excised tumor tissue 125 in the sample cartridge 137. Ultrasound waves can be recorded by an ultrasound transducer 129 array. Through X-Y scanning stage 123 controlled by the host-control computer 1000 through any suitable connection, such as a USB cable. 3D images of the excised tumor tissue will be acquired and displayed on the user interface 114. The particular devices identified here are for demonstration purposes and the scope of the disclosure should not be limited to these devices.

The imaging chamber 105 is designed to fulfill automatic three-dimensional tumor tissue capturing and can be any suitable size. In one exemplary embodiment, the imaging chamber 105 can have the dimensions of approximately 330 mm×260 mm×380 mm. The imaging chamber can comprise an imaging probe, an X-Y computer numerical control (CNC) stage, a vertical elevation stage, a tissue-compressing unit, and a water drainage unit. In one exemplary embodiment, the imaging chamber can be filled with a fluid, such as water.

Once tumorous tissue is resected, it can first be rinsed with a saline solution, such as about a 0.9% saline solution. The tumor can then be placed on top of a sample cartridge. The cartridge can comprise of a foam for holding the tissue, absorbing the sound wave, and cushioning the impact due to the compressing. Alternatively or in addition to the foam, a coupling medium can be used to support the tissue sample. In this exemplary embodiment of the imaging chamber, the top cover of the chamber can then be opened via a handle. The sample cartridge can then be inserted into the scanning holder. The tissue will be oriented on the cartridge according to the standard instructions. The top cover can then be closed, and the vertical elevation stage can be used to adjust the height of the cartridge, so as to make a close contact between the tissue and a plastic wrap or film, which is used to hold the coupling medium in the top and compress the coupling medium on top of the sample. The plastic film can be composed of polyvinyl chloride, polyethylene, polyvinylidene fluoride, silicone, polyvinylidene chloride, or other similar material. Upon laser light excitation from the fiber bundle, which in one exemplary embodiment can be about 5×2 mm$^2$, ultrasound waves can be generated from the excised tumor tissue. The ultrasound waves can then be recorded by an ultrasound transducer array with about 128 elements and about a pre-determined frequency. In one embodiment the pre-determined frequency is a 18 MHz center frequency. The ultrasound transducer is connected to the ultrasound source and data acquisition subsystem, using any suitable connector 135, such as a Cannon HDI-format ZIF connector. Through X-Y CNC stage controlled by the host-control computer, three dimensional (3D) imaging of the excised tumor tissue can be acquired.

Figure 3A:
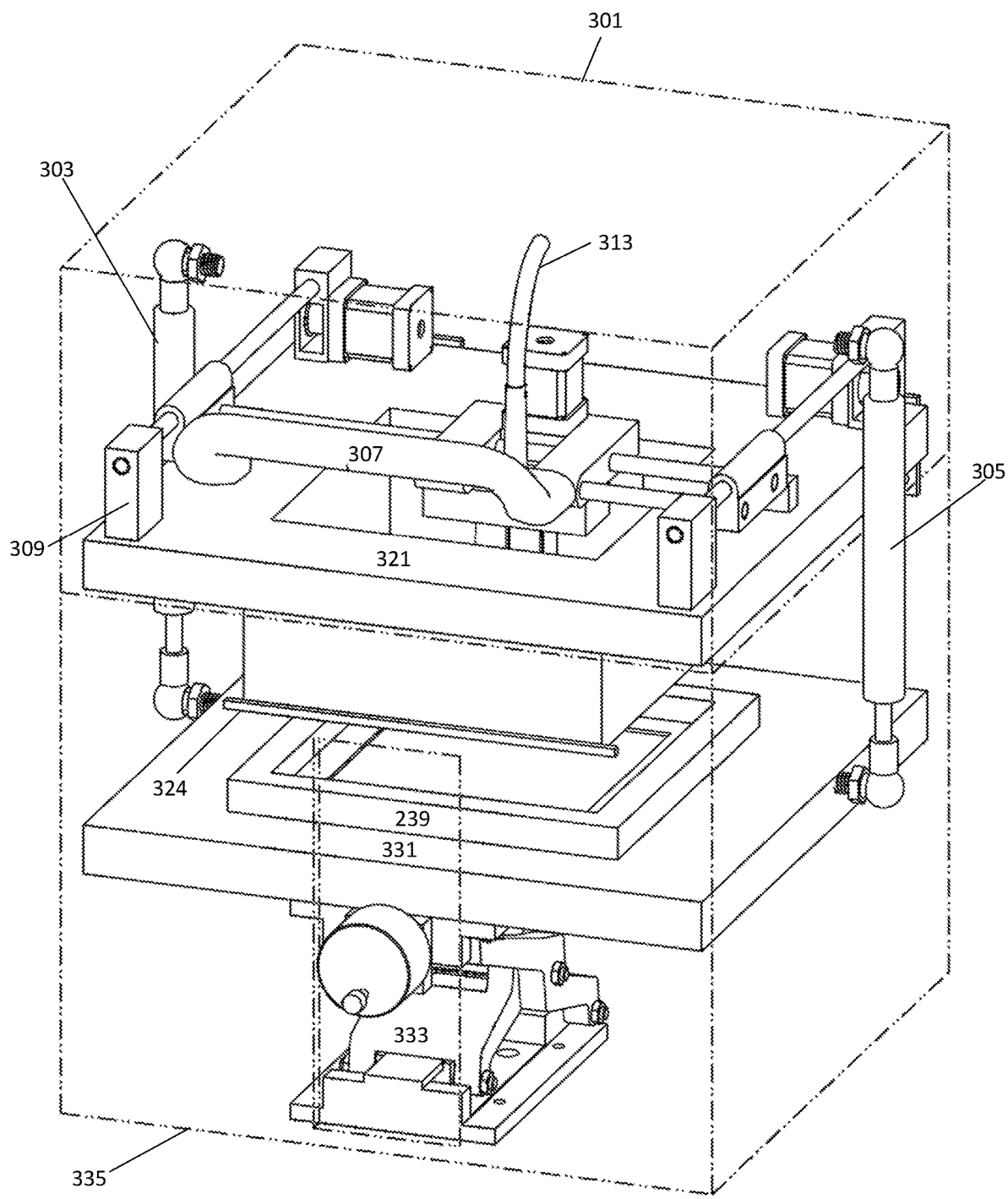
FIG. 3A is an illustration of an exemplary embodiment of an imaging chamber.
Figure 3B:
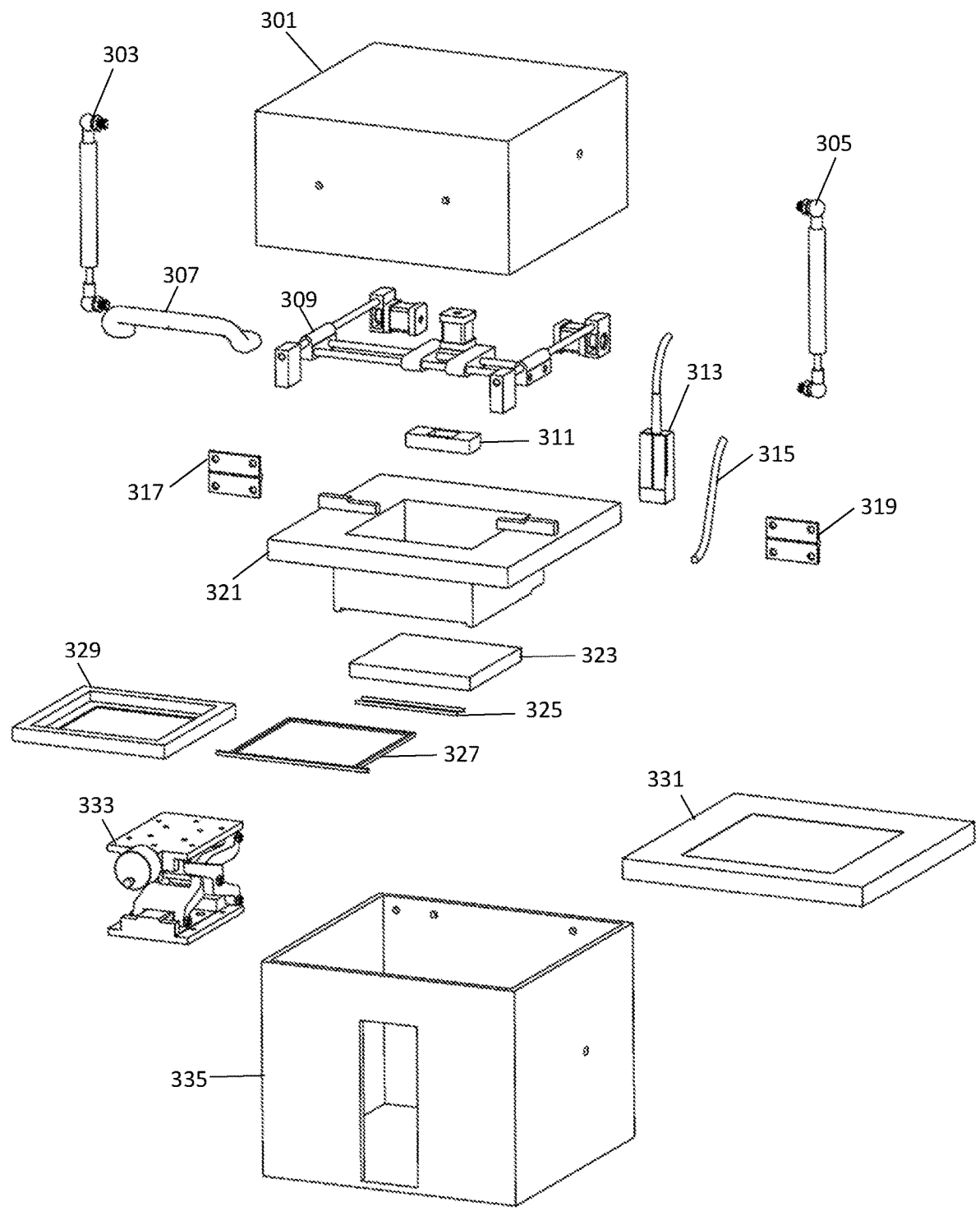
FIG. 3B is an illustration of an exemplary embodiment of components of an imaging chamber.

Referring to FIG. 3A is a trimetric view of the imaging chamber. FIG. 3B is an illustration of an exemplary embodiment of the various components that can comprise and imaging chamber. The chamber can comprise a top cover 301, gas springs 303, 305, hand handle 307, CNC stage 309, imaging probe holder 311, imaging probe 313, water drainage tube 315, surface mount hinges 317, 319, compression plate 321, water illustration 323, tissue-pressing rod 325, changeable plate with a plastic wrap or film 327, changeable tissue cartridge 329, cartridge holder 331, vertical elevation stage 333, and bottom cover 335.

The sample chamber can be comprised of three parts: an imaging probe 313 with the X-Z scanning stage 309, a sample cartridge 329 with pre-filled ultrasound gel, and a water tank or sample cartridge holder 331 with the imaging window. After the tumor tissue is removed from the patient, it can be transferred to the sample cartridge. A pre-filled support medium or coupling medium can be used to fix the tissue in position for imaging. In one exemplary embodiment the support medium can be an ultrasound gel. The sample cartridge can then be placed in the water tank or sample cartridge holder. In one exemplary embodiment, the water tank or sample cartridge holder dimension can be about 240 mm long by about 140 mm wide by about 150 mm high. Clinical saline solution can be added to the cartridge and water tank, and can act as a coupling medium for the imaging probe.

Figure 4A:
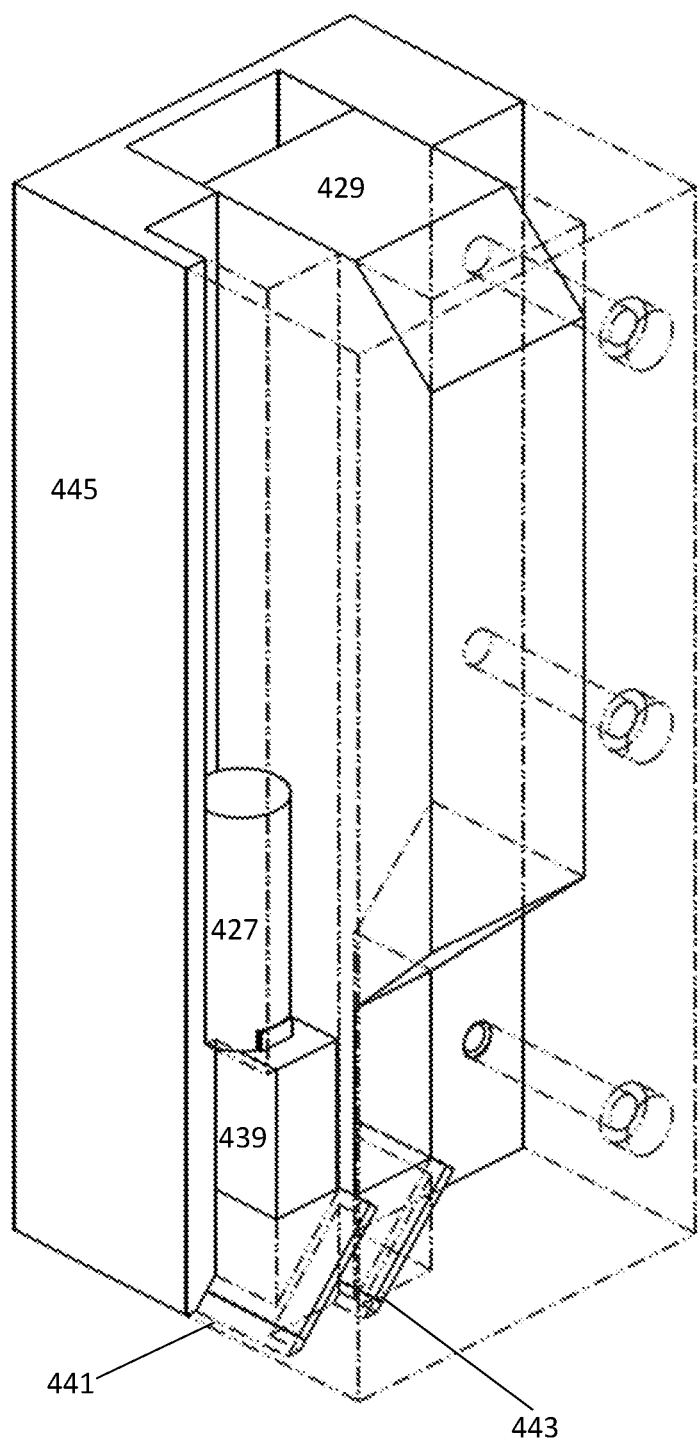
FIG. 4A is an illustration of an exemplary embodiment of an imaging probe.

FIG. 4 shows the detail design of one exemplary embodiment of an imaging probe. This collinear design ensures the laser light and ultrasound wave share the same pathway to the sample. The laser light coming through the fiber bundle 427 can first be collimated via one or multiple cylindrical lenses 439. The collimated light can then be reflected by about a 45 degree mirror 441 with high-reflection coating. In one embodiment, the mirror can be about 1 inch diameter, about 0.25 inch thickness, and have about 99.9% reflectivity at about 1197 nm.

Upon laser light excitation from the fiber bundle 427 terminal, the ultrasound waves are generated from the excised tumor tissue in the sample cartridge. The ultrasound waves are can be recorded by an ultrasound transducer array 429. One exemplary embodiment of the ultrasound transducer array can have about 128 elements and about 18 MHz center frequency. The ultrasound transducer 429 is connected to the ultrasound source and data acquisition subsystem. Any suitable connection can be used, such as a Cannon HDI-format ZIF connector. The X-Z scanning stage controlled by the host-control computer through any suitable connection, such as a USB cable. 3D imaging of the sensing face of the excised tumor tissue will be acquired. After one-face scanning, the cartridge can be flipped 180 degrees. A second scanning can then be performed for the other face. In this way, the 3D imaging of the whole sample can be generated.

Each specimen can be fixed with a coupling medium within the sample cartridge, such as 2.5% H2O-agarose gel. In one exemplary embodiment, a gel or other coupling medium can be pre-loaded into the cartridge during the packaging and preparation of the cartridge. Upon receiving a cartridge, a physician would not need to do any preparation of the cartridge due to the pre-loaded nature of the cartridge with a coupling medium and ready to accept any samples needed to be screened by the system. A saline solution can be added in the sample holder as the ultrasonic coupling medium. After the transducer is immersed into the saline solution, the US/PA imaging can obtain with about a 100 µm step size for the whole specimen top surface or first face. The specimen can be flipped, and the bottom surface or second face can then be imaged. This can also be accomplished by flipping the cartridge or rotating the cartridge within the imaging chamber to ensure the entire sample is properly imaged.

By employing a sliding Gaussian window with about 0.4 mm in width along each channel of US/RF signal, averaged RF spectrum of each window could be obtained and then exported to tissue classification using k-means clustering algorithm, producing a 3-type tissue map. Together with the dual-color PA images, a tissue map can be produced with different color coding representing different types of tissue. In one exemplary embodiment, a modified back projection algorithm can be used to construct the 3D image.

Figure 4B:
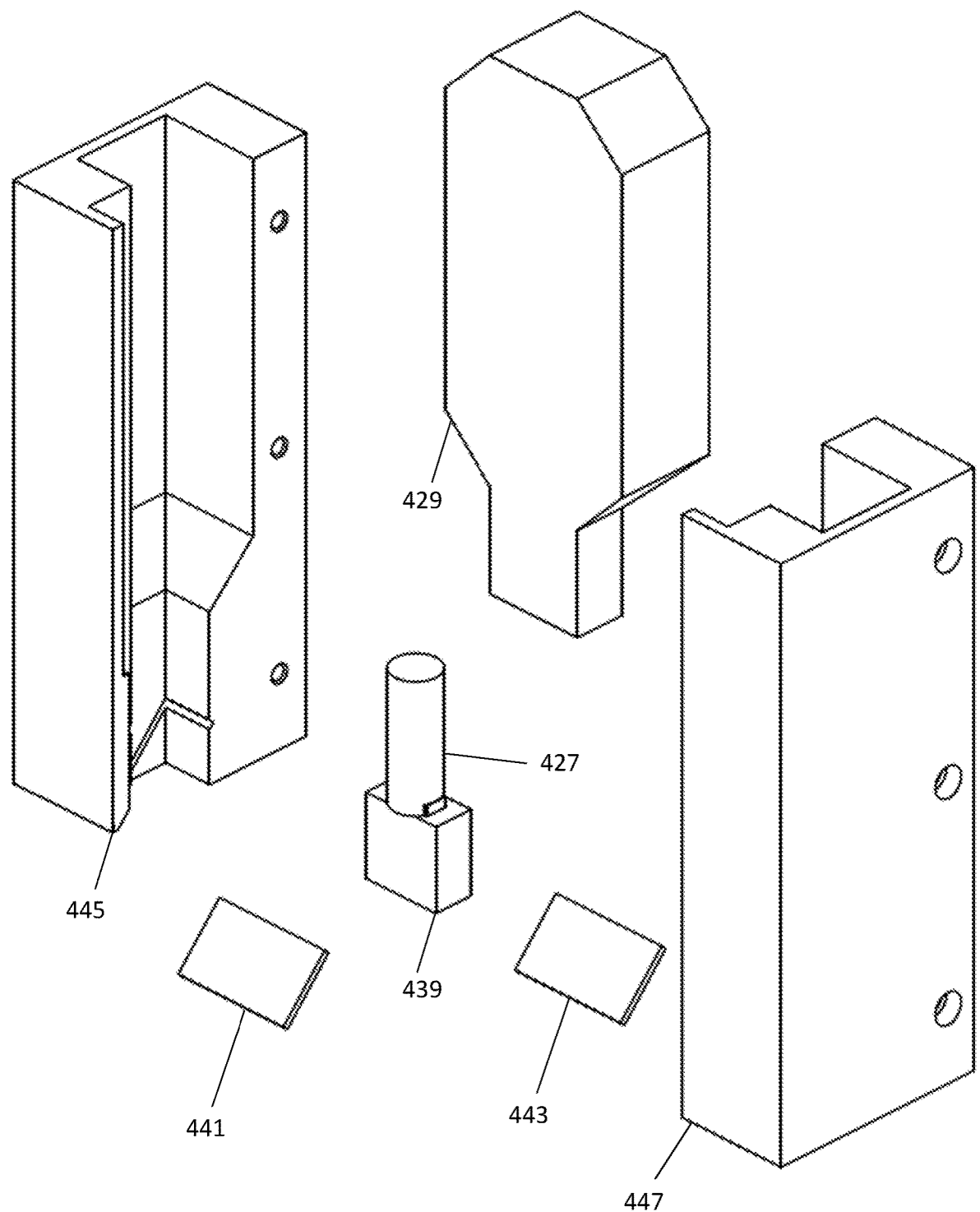
FIG. 4B is an illustration of an exemplary embodiments of various components of an imaging probe.

The sample cartridge can be in any suitable shape to facilitate in supporting a sample that will be analyzed by the imaging system. One exemplary embodiment of the sample cartridge can be a pyramidal shape. The pyramidal shape allows the cartridge to support various sized samples. The inverted pyramidal shape helps to support the sample within the cartridge along with the coupling medium. This allows for the imaging system to better analyze the sample in its totality without having to adjust the cartridge or sample after the sample has been placed inside the cartridge. This shape helps to provide an even surface for imaging the first and second sample face. The imaging probe is used to acquire both the conventional ultrasound images and photoacoustic images. In one exemplary embodiment the imaging probe can be 103×35×35 mm$^3$. As shown in FIG. 4B, the imaging probe can be comprised of a transducer array 429, a fiber bundle 427, a cylindrical lens 439, and two glass slides 441, 443. The fiber bundle can deliver the laser light from the laser subsystem. The cylindrical lens can be applied to weakly focus the light to the tissue surface to generate a photoacoustic signal. One exemplary embodiment of a collinear imaging probe comprises a transducer array that is held within a cover mount assembly 445, 447. The fiber bundle and cylindrical lens is located within the cover mount assembly 445, 447 and glass slides 441, 443 are located proximate to the cylindrical lens 439 and transducer array 429.

Figure 5:
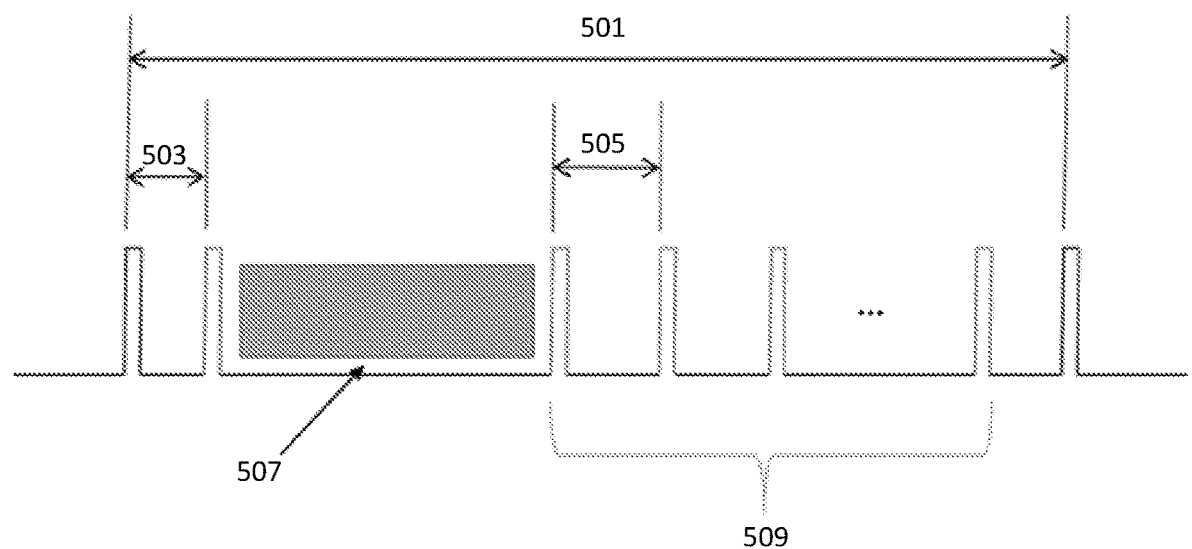
FIG. 5 is the data flow of the various signal acquisition phases of the present invention.

The data flow of the system according to the present disclosure is shown in FIG. 5. In an exemplary embodiment, the function generator can output about a 10 Hz, 10 µs transistor-transistor logic (TTL) signal to trigger a flashlamp of the Nd:YAG laser and the delay generator over a pre-determined period of time 501, such as 100 ms. The delay generator can output two 10 Hz, 10 µs TTL signals with time delay 503 of about 299 μs to trigger a Q-switch of the Nd:YAG laser and data acquisition subsystem simultaneously. The photoacoustic signal 507 can then be acquired with the ultrasound transducer. Once the acquisition is complete, the ultrasound mode works immediately. The ultrasound transducer can then send ultrasound pulses into the sample to form a focus spot at a pre-determined depth. The ultrasound transducer can then receive echo information 509 immediately, and store the information in radio frequency data format. With an inherent delay 505 of about 327 μs, the transducer sends another ultrasound pulses to translate the focus spot in the sample laterally by 0.1 mm, and records the data in the same way. The focus spot is sequentially translated by about 0.1 mm for about 128 times (transducer element numbers) in total.

Figure 6:
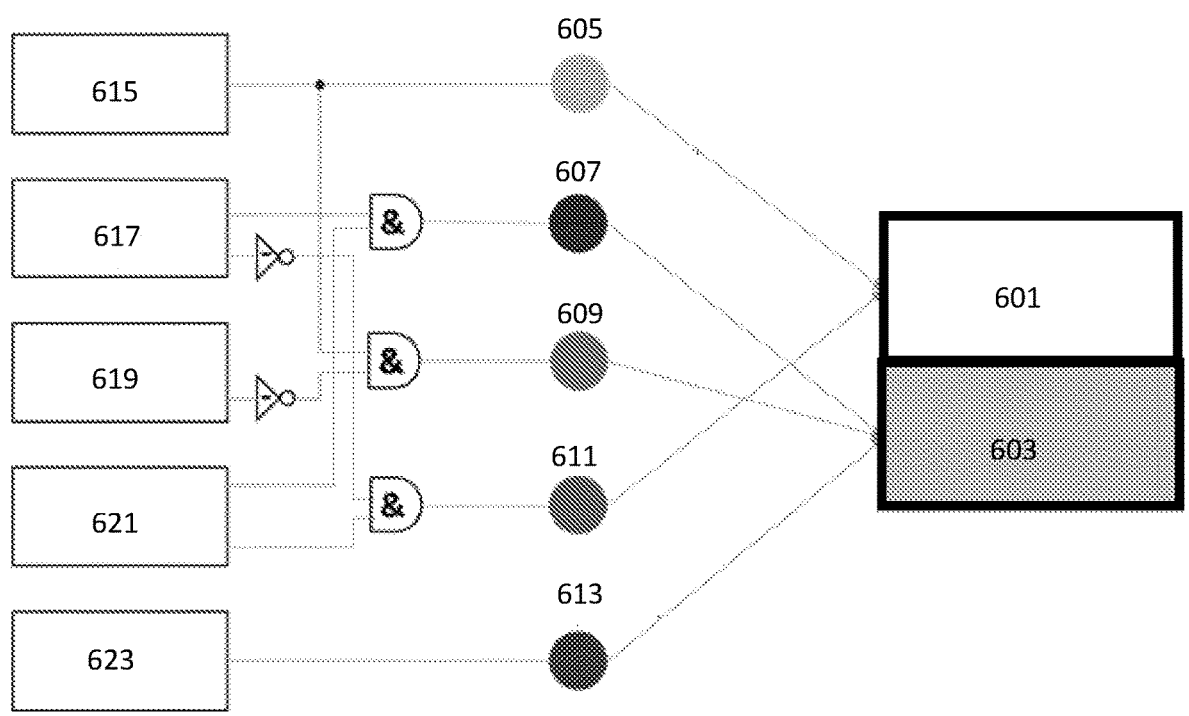
FIG. 6 is a diagram of an analysis scheme to differentiate normal and tumor tissue.

The PA image with RF spectrum analysis of US signal can then be combined to synergistically extract comprehensive tissue-specific information. FIG. 6 shows the diagram for the analysis scheme to differentiate normal or non-cancerous tissue 601 and tumorous or cancerous tissue 603. Photoacoustic By employing a sliding Gaussian window with about 0.4 mm width along each channel of US RF signal, averaged RF spectrum of each window could be obtained and then exported to tissue classification using k-means clustering algorithm, producing a 3-type tissue map. Together with the dual-color PA images, we produced a tissue map with different color coding representing different types of tissue. Applying the classification scheme shown in FIG. 6, the five classification comprising fat 605, angiogenesis 607, calcification 609, fibrosis 611, and malignant 613 contrasts can further be divided into cancer 603 vs. non-cancer 601 category, providing basis for positive/negative margin determination. Accordingly, a tumor can be differentiated from major types of normal tissue based on the contrasts provided by two-color PA images and RF spectrum analysis of US images. These can include PA-fat contrasts 615, PA-hemoglobin contrasts 617, among other PA and RF spectrum contrasts 619, 621, 623.

Figure 7:
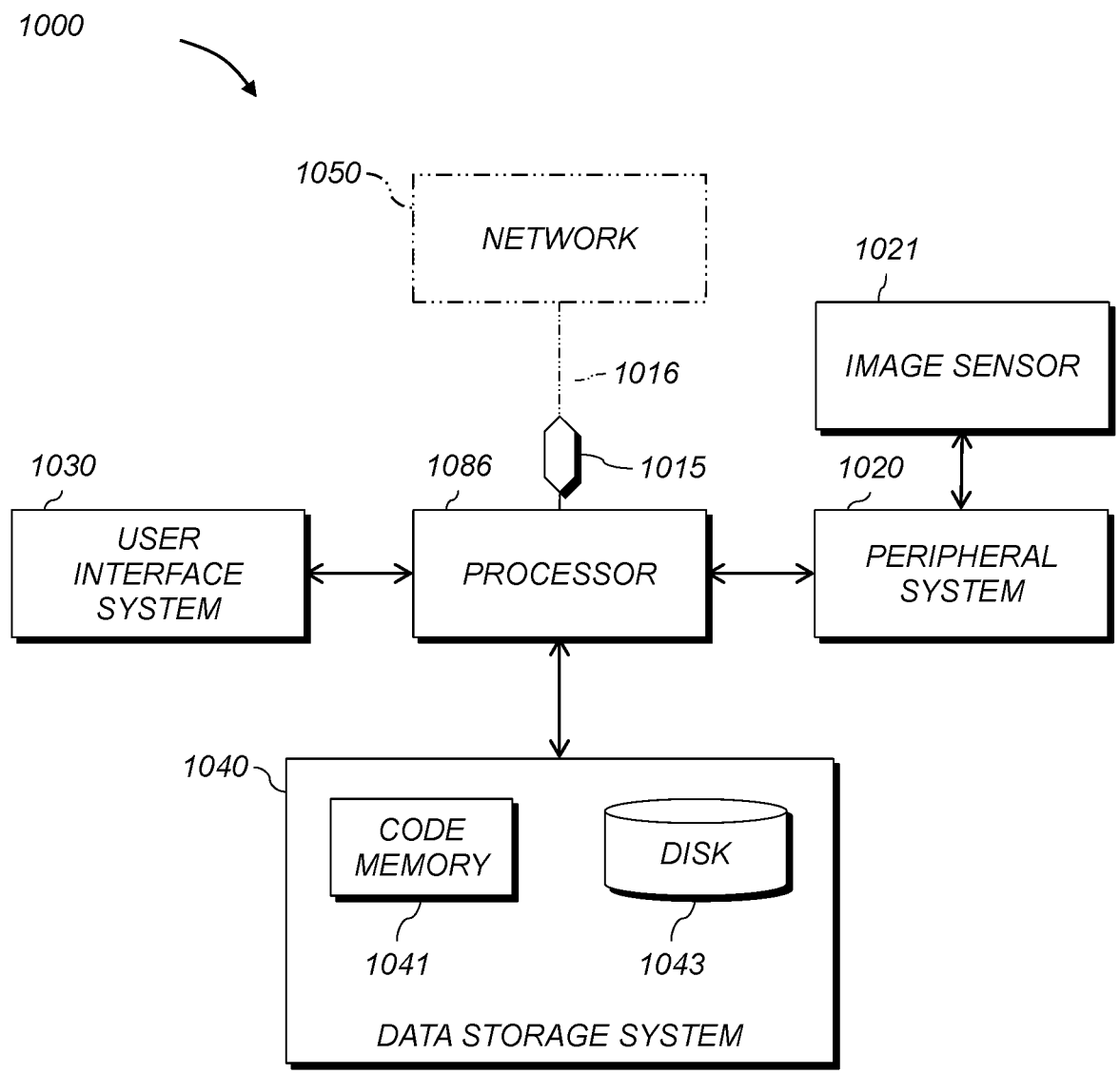
FIG. 7 is a high-level diagram showing the components of an exemplary data-processing system for analyzing data and performing other analyses of tissue samples.

Referring to FIG. 7, a high-level diagram showing the components of an exemplary data processing system 1000 for analyzing data and performing other analyses described herein, and related components is provided. The system includes a processor 1086, a peripheral system 1020, a user interface system 1030, and a data storage system 1040. The peripheral system 1020, the user interface system 1030 and the data storage system 1040 are communicatively connected to the processor 1086. Processor 1086 can be communicatively connected to network 1050 (shown in phantom), e.g., the Internet or a leased line, as discussed below. The imaging and 3D point data described in the Papers may be obtained using imaging sensors 1021 and/or displayed using display units (included in user interface system 1030) which can each include one or more of systems 1086, 1020, 1030, 1040, and can each connect to one or more network(s) 1050.

Processor 1086, and other processing devices described herein, can each include one or more microprocessors, microcontrollers, field-programmable gate arrays (FPGAs), application specific integrated circuits (ASICs), programmable logic devices (PLDs), programmable logic arrays (PLAs), programmable array logic devices (PALS), or digital signal processors (DSPs).

Processor 1086 can implement processes of various aspects described herein. Processor 1086 can be or include one or more device(s) for automatically operating on data, e.g., a central processing unit (CPU), microcontroller (MCU), desktop computer, laptop computer, mainframe computer, personal digital assistant, digital camera, cellular phone, smartphone, or any other device for processing data, managing data, or handling data, whether implemented with electrical, magnetic, optical, biological components, or otherwise. Processor 1086 can include Harvard-architecture components, modified-Harvard-architecture components, or Von-Neumann-architecture components.

The phrase "communicatively connected" includes any type of connection, wired or wireless, for communicating data between devices or processors. These devices or processors can be located in physical proximity or not. For example, subsystems such as peripheral system 1020, user interface system 1030, and data storage system 1040 are shown separately from the data processing system 1086 but can be stored completely or partially within the data processing system 1086.

The peripheral system 1020 can include one or more devices configured to provide digital content records to the processor 1086. For example, the peripheral system 1020 can include digital still cameras, digital video cameras, cellular phones, or other data processors. The processor 1086, upon receipt of digital content records from a device in the peripheral system 1020, can store such digital content records in the data storage system 1040.

The user interface system 1030 can include a mouse, a keyboard, another computer (connected, e.g., via a network or a null-modem cable), or any device or combination of devices from which data is input to the processor 1086. The user interface system 1030 also can include a display device, a processor-accessible memory, or any device or combination of devices to which data is output by the processor 1086. The user interface system 1030 and the data storage system 1040 can share a processor-accessible memory.

In various aspects, processor 1086 includes or is connected to communication interface 1015 that is coupled via network link 1016 (shown in phantom) to network 1050. For example, communication interface 1015 can include an integrated services digital network (ISDN) terminal adapter or a modem to communicate data via a telephone line; a network interface to communicate data via a local-area network (LAN), e.g., an Ethernet LAN, or wide-area network (WAN); or a radio to communicate data via a wireless link, e.g., WiFi or GSM. Communication interface 1015 sends and receives electrical, electromagnetic or optical signals that carry digital or analog data streams representing various types of information across network link 1016 to network 1050. Network link 1016 can be connected to network 1050 via a switch, gateway, hub, router, or other networking device.

Processor 1086 can send messages and receive data, including program code, through network 1050, network link 1016 and communication interface 1015. For example, a server can store requested code for an application program (e.g., a JAVA applet) on a tangible non-volatile computer-readable storage medium to which it is connected. The server can retrieve the code from the medium and transmit it through network 1050 to communication interface 1015. The received code can be executed by processor 1086 as it is received, or stored in data storage system 1040 for later execution.

Data storage system 1040 can include or be communicatively connected with one or more processor-accessible memories configured to store information. The memories can be, e.g., within a chassis or as parts of a distributed system. The phrase "processor-accessible memory" is intended to include any data storage device to or from which processor 1086 can transfer data (using appropriate components of peripheral system 1020), whether volatile or non-volatile; removable or fixed; electronic, magnetic, optical, chemical, mechanical, or otherwise. Exemplary processor-accessible memories include but are not limited to: registers, floppy disks, hard disks, tapes, bar codes, Compact Discs, DVDs, read-only memories (ROM), erasable programmable read-only memories (EPROM, EEPROM, or Flash), and random-access memories (RAMS). One of the processor-accessible memories in the data storage system 1040 can be a tangible non-transitory computer-readable storage medium, i.e., a non-transitory device or article of manufacture that participates in storing instructions that can be provided to processor 1086 for execution.

In an example, data storage system 1040 includes code memory 1041, e.g., a RAM, and disk 1043, e.g., a tangible computer-readable rotational storage device such as a hard drive. Computer program instructions are read into code memory 1041 from disk 1043.

Processor 1086 then executes one or more sequences of the computer program instructions loaded into code memory 1041, as a result performing process steps described herein. In this way, processor 1086 carries out a computer implemented process. For example, steps of methods described herein, blocks of the flowchart illustrations or block diagrams herein, and combinations of those, can be implemented by computer program instructions. Code memory 1041 can also store data, or can store only code.

Various aspects described herein may be embodied as systems or methods. Accordingly, various aspects herein may take the form of an entirely hardware aspect, an entirely software aspect (including firmware, resident software, micro-code, etc.), or an aspect combining software and hardware aspects These aspects can all generally be referred to herein as a "service," "circuit," "circuitry," "module," or "system."

Furthermore, various aspects herein may be embodied as computer program products including computer readable program code stored on a tangible non-transitory computer readable medium. Such a medium can be manufactured as is conventional for such articles, e.g., by pressing a CD-ROM. The program code includes computer program instructions that can be loaded into processor 1086 (and possibly also other processors), to cause functions, acts, or operational steps of various aspects herein to be performed by the processor 1086 (or other processor). Computer program code for carrying out operations for various aspects described herein may be written in any combination of one or more programming language(s), and can be loaded from disk 1043 into code memory 1041 for execution. The program code may execute, e.g., entirely on processor 1086, partly on processor 1086 and partly on a remote computer connected to network 1050, or entirely on the remote computer.

Experimental Data and Results

FIGS. 8A-E show the representative images taken by the system of the present disclosure and the associated histopathology results. The tumor specimen (FIG. 8D) was excised from a 68-year-old female patient diagnosed with invasive ductal carcinoma. The B-mode US image shown in FIG. 8A identifies the tissue morphology. Photoacoustic imaging at 1197 nm (FIG. 8B) maps lipid distribution with 3 mm imaging depth, indicating the healthy tissue.

Based on H&E stained section (FIG. 8C), the area without fat is assigned to be cancerous tissue 802 or connective tissue 801, which can be further distinguished by RF spectrum analysis based on their distinctive frequency responses. With an X-Y translation stage, the sample is scanned from medial to lateral direction, as shown by a black arrow in FIG. 8D.

Figure 8:
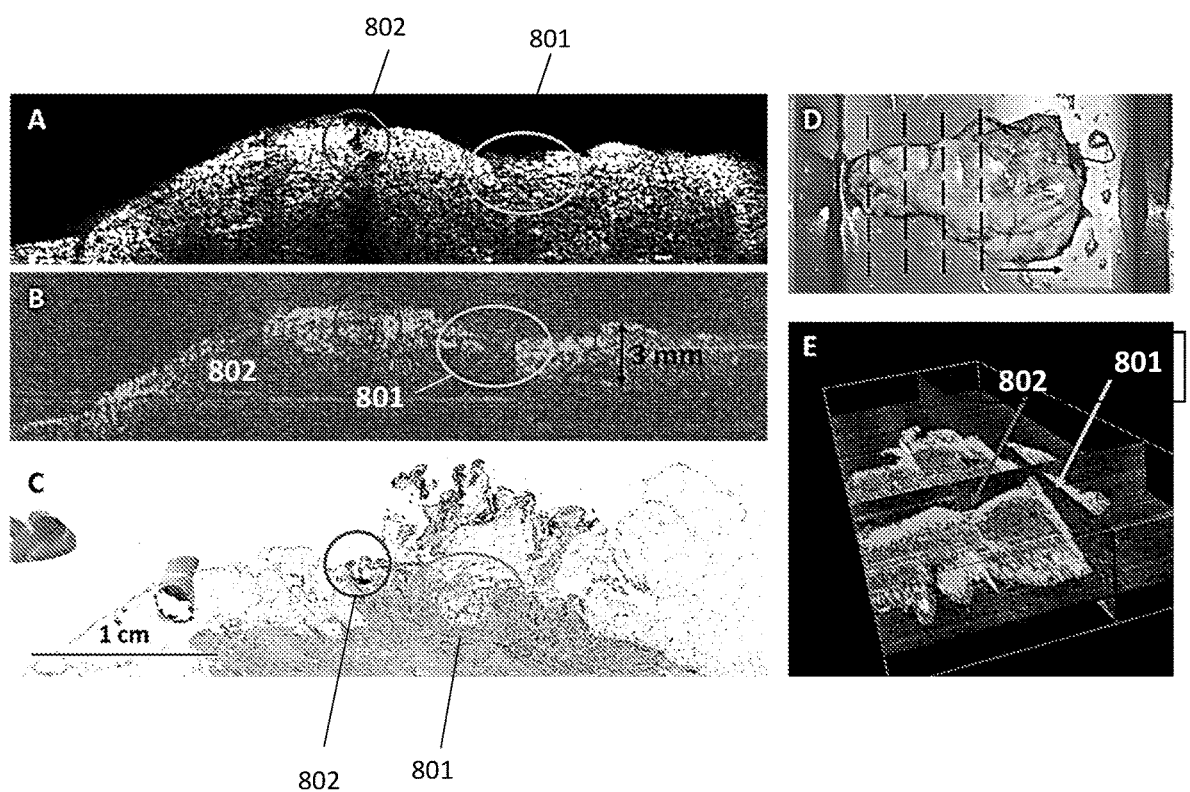
FIG. 8A is ultra sound image of human tissue morphology.
FIG. 8B is photo acoustic image of human tissue morphology.
FIG. 8C is an image of human tissue after being H&E stained.
FIG. 8D is an image of a tumor specimen removed from a patient for testing the present invention.
FIG. 8E is an image generated by the present invention to distinguish connective tissue and cancerous tissue.

The 3D imaging in less than about 4 minutes generated by present system is shown in FIG. 8E, showing the tissue boundary, fat tissue, connective tissue 801, and cancerous tissue 802. The cancerous tissue intrudes to the surface of the excised specimen, indicating this is a positive margin, which is consistent with the histopathology results. The system according to the present disclosure has accomplished about 100% sensitivity, and about 85% specificity in several tens of samples.

In order to confirm the margin status, excised breast tumor tissues were marked with paints of different colors representing different areas. The marked tissue was cut into several blocks to accommodate the cassette size. Usually, one section from one block was picked for the H&E staining, which was evaluated by a pathologist to determine the margin status. The pathologist was blinded to images from the system of the present disclosure and results.

This application is intended to cover adaptations or variations of the present subject matter. It is to be understood that the above description is intended to be illustrative, and not restrictive. The scope of the present subject matter should be determined with reference to the appended claims, along with the full scope of legal equivalents to which such claims are entitled.

What is claimed is:

1. A multimodal ultrasound/photoacoustic tumor margin detection system, comprising:
    an imaging and system control console, including:
        an ultrasound and data acquisition subsystem including an ultrasound transmitter and an ultrasound receiver configured to transmit and receive ultrasonic energy, and
        a host-control computer configured to provide a function generator function and a delay generation function;
    a laser subsystem, comprising at least one laser coupled to a fiber bundle;
    an imaging probe, comprising an ultrasound transducer configured to be excited by the ultrasound transmitter of the ultrasound and data acquisition subsystem and provide data to the ultrasound receiver of the ultrasound and data acquisition subsystem, and an optical channel coupled to the fiber bundle that provides the optical energy to a tissue sample under investigation; and
    an imaging chamber, wherein the imaging chamber houses a X-Z scanning stage for holding and moving a tissue sample cartridge or the imaging probe within the imaging chamber, wherein the tissue sample cartridge has a support medium, wherein the optical energy and the ultrasonic energy are transmitted to the tissue sample in the tissue sample cartridge, wherein the tissue sample generates one or more signals that is obtained by the imaging probe and used for generating one or more images of the tissue sample.

2. The system of claim 1, wherein said optical energy and the ultrasonic energy share the same path through the imaging probe.

3. The system of claim 1, wherein the optical energy can be collinearly aligned with the ultrasonic energy within the imaging probe.

4. The system of claim 1, wherein said the laser is a Raman laser, wherein the optical energy is transmitted through the fiber bundle and collimated by a lens before being transmitted to the tissue sample.

5. The system of claim 1, wherein said laser is a Nd:YAG pumped Raman.

6. The system of claim 1, wherein the support medium in the tissue sample cartridge absorbs the impact of the ultrasonic energy directed toward the tissue sample and cushions the tissue sample from the compression applied during the imaging of the tissue sample.

7. The system of claim 6, wherein said imaging chamber further comprises a tissue-compressing unit including a plastic film configured to compress a surface of the tissue sample on the tissue sample cartridge.

8. The system of claim 7, wherein said plastic film is part of a changeable plate on the bottom surface of the changeable plate, wherein the plastic film can be made of polyvinyl chloride, polyethylene, polyvinylidene fluoride, silicone, or polyvinylidene chloride.

9. The system of claim 1, wherein said laser subsystem further comprises a half wave plate and a quarter wave plate, wherein said half wave plate and a polarizer are configured to adjust optical energy, and wherein said quarter wave plate is configured to protect the laser from back-reflection.

10. The system of claim 1, wherein said laser subsystem further comprises a plurality of mirrors, comprising a first mirror, a second mirror, a third mirror, a fourth mirror, a fifth mirror, and a sixth mirror.

11. The system of claim 10, wherein said first mirror, said fourth mirror, said fifth mirror and said sixth mirror are positioned at a 45 degree angle and arranged in a configuration to direct the optical energy emitted by the laser.

12. A multimodal ultrasound/photoacoustic tumor margin detection system for examining a tissue sample, comprising:
   a) an imaging and system control console, including:
      an ultrasound and data acquisition subsystem including an ultrasound transmitter and an ultrasonic receiver, and
      a host-control computer configured to provide a function generator function and
      a delay generation function;
   b) a laser subsystem, comprising
      at least one laser for emitting an optical energy, wherein the laser is coupled to a fiber bundle,
      a $Ba(NO_3)_2$ Raman crystal,
      a half wave plate,
      a polarizer;
      a quarter wave plate, and
      a plurality of mirrors, comprising a first mirror, a second mirror, a third mirror, a fourth mirror, a fifth mirror, and a sixth mirror, wherein said plurality of mirrors are arranged in a configuration to direct the optical energy emitted by said laser;
   c) an imaging probe, comprising:
      an ultrasound transducer configured to be excited by the ultrasound transmitter of the ultrasound and data acquisition subsystem and provide data to the ultrasound receiver of the ultrasound and data acquisition subsystem,
      an optical channel coupled to the fiber bundle, wherein the fiber bundle provides the optical energy from the laser to the tissue sample under investigation, wherein the optical energy from the laser and the ultrasonic energy share the same path through the imaging probe; and
   d) an imaging chamber, comprising:
      an openable top cover;
      an X-Z scanning stage within the imaging chamber, wherein the X-Z scanning stage to holds a tissue sample cartridge or the imaging probe for interrogation of the tissue sample, wherein the tissue sample cartridge contains a medium for supporting the tissue sample, and
      a plastic film to compress a surface of the tissue sample and transmit the optical energy and the ultrasonic energy, wherein the plastic film can be made of polyvinyl chloride, polyethylene, polyvinylidene fluoride, silicone, or polyvinylidene chloride, wherein the optical energy from the laser and the ultrasonic energy is provided to the tissue sample and the imaging probe obtains one or more signals generated by the tissue sample, wherein the one or more signals are used by the imaging and system control console to generate one or more images of the tissue sample, wherein upon closing the top cover the plastic film can compress the tissue sample on the tissue sample cartridge for imaging.

13. The multimodal ultrasound/photoacoustic tumor margin detection system of claim 1, wherein a first surface of the tissue sample within the tissue sample cartridge is scanned using the imaging probe, and the tissue sample is reoriented relative to the ultrasound transducer of the imaging probe and a second surface of the tissue sample within the tissue sample cartridge is scanned by the imaging probe, wherein one or more signals obtained from the scans of the first surface and the second surface are used by the system to generate the images, wherein the images generated by the system are two dimensional cross-sectional images.

14. The multimodal ultrasound/photoacoustic tumor margin detection system of claim 13, the one or more signals can be at least one of the following:
   a photoacoustic signal, or
   a ultrasonic signal.

15. The multimodal ultrasound/photoacoustic tumor margin detection system of claim 14, wherein the system classifies one or more portions of the tissue sample as tumorous or non-tumorous based at least one of the following:
   the photoacoustic signals, or
   the ultrasonic signals.

16. The multimodal ultrasound/photoacoustic tumor margin detection system of claim 15, wherein the photoacoustic signals and ultrasonic signals are generated from the tissue sample and captured by the ultrasound transducer.

17. The multimodal ultrasound/photoacoustic tumor margin detection system of claim 13, wherein the imaging chamber further includes a compression plate and a tissue-pressing rod to compress the tissue sample during imaging, wherein the two-dimensional cross-sectional images can be used to generate a 3D volumetric image of the tissue sample.

18. The multimodal ultrasound/photoacoustic tumor margin detection system for examining a tissue sample of claim 12, wherein a first surface of the tissue sample within the tissue sample cartridge is scanned using the imaging probe and the tissue sample is reoriented relative to the ultrasound transducer and a second surface of the tissue sample within the tissue sample cartridge is scanned, wherein a dataset is obtained from the scans of the first surface and the second surface are used by the system to generate the image, wherein the images generated by the system be a two dimensional cross-sectional images.

19. The multimodal ultrasound/photoacoustic tumor margin detection system for examining a tissue sample of claim 18, wherein the system classifies one or more portions of the tissue sample as tumorous or non-tumorous based at least one of the following:
   the photoacoustic signals, or
   the ultrasonic signals.

20. The multimodal ultrasound/photoacoustic tumor margin detection system for examining a tissue sample of claim 19, wherein the imaging chamber further includes a compression plate and a tissue-pressing rod to compress the tissue sample during imaging, wherein the two-dimensional cross-sectional images can be used to generate a 3D volumetric image of the tissue sample.

* * * * *